(12) United States Patent
Harder et al.

(10) Patent No.: US 12,085,563 B2
(45) Date of Patent: Sep. 10, 2024

(54) FLOW ASSAY ANALYZER

(71) Applicant: Kenota Inc., Kitchener (CA)

(72) Inventors: Christopher J. Harder, Elmira (CA);
David Andrew McMullin, Ottawa (CA); Eric Blondeel, Waterloo (CA);
Kien Vu, Nepean (CA)

(73) Assignee: Kenota Inc., Kitchener (CA)

( * ) Notice: Subject to any disclaimer, the term of this patent is extended or adjusted under 35 U.S.C. 154(b) by 738 days.

(21) Appl. No.: 17/311,864

(22) PCT Filed: Dec. 20, 2019

(86) PCT No.: PCT/CA2019/051873
§ 371 (c)(1),
(2) Date: Jun. 8, 2021

(87) PCT Pub. No.: WO2020/124255
PCT Pub. Date: Jun. 25, 2020

(65) Prior Publication Data
US 2022/0042983 A1 Feb. 10, 2022

(51) Int. Cl.
*G01N 21/05* (2006.01)
*G01N 33/543* (2006.01)
(Continued)

(52) U.S. Cl.
CPC ....... *G01N 33/54388* (2021.08); *G01N 21/05* (2013.01); *G01N 35/1009* (2013.01); *G01N 35/1065* (2013.01); *G01N 35/1081* (2013.01); *G01N 2035/00356* (2013.01); *G01N 2035/00455* (2013.01); *G01N 2035/1025* (2013.01)

(58) Field of Classification Search
CPC ............. G01N 33/54388; G01N 21/05; G01N 35/1009; G01N 35/1065; G01N 35/1081; G01N 2035/00356; G01N 2035/00455; G01N 2035/1025; G01N 2035/00108; G01N 35/04; G01N 35/1095; G01N 2035/0427; G01N 2035/0436; G01N 2035/0465; G01N 33/558; G01N 2035/0425; B01L 2200/025; B01L 2200/028; B01L 2200/04;
(Continued)

(56) References Cited

U.S. PATENT DOCUMENTS 8,883,509 B2  11/2014  Lemme et al.
9,212,995 B2  12/2015  Moll et al.
(Continued)

FOREIGN PATENT DOCUMENTS

CN   106018855 A   8/2017
DE   298063034     10/1998
(Continued)

*Primary Examiner* — Jill A Warden
*Assistant Examiner* — John McGuirk

(57) ABSTRACT

Described is a lateral flow high throughput assay device analyzer for preparing and analyzing a plurality of lateral flow assay samples. The analyzer comprises a cartridge stage for supporting an assay cartridge, an elevation adjustment mechanism, and a translation adjustment mechanism for aligning the cartridge stage and assay cartridge relative to a vertical support structure, fluid metering device, and detection device for high throughput lateral flow assay analysis.

19 Claims, 9 Drawing Sheets

(51) Int. Cl.
*G01N 35/00* (2006.01)
*G01N 35/10* (2006.01)

(58) Field of Classification Search
CPC ..... B01L 2300/0663; B01L 2300/0825; B01L 3/50273; B01L 9/527; B65D 83/0418
See application file for complete search history.

(56) References Cited

U.S. PATENT DOCUMENTS

| | | |
|---|---|---|
| 9,377,476 B2 | 6/2016 | Cong et al. |
| 2004/0208785 A1* | 10/2004 | Seto ................. G01N 33/48757 422/63 |
| 2007/0184546 A1 | 8/2007 | Farrelly et al. |
| 2009/0293644 A1 | 12/2009 | Sancho |
| 2011/0020178 A1 | 1/2011 | Clinton et al. |
| 2014/0073043 A1 | 3/2014 | Holmes |
| 2015/0276566 A1 | 10/2015 | Berntsen et al. |
| 2018/0088141 A1 | 3/2018 | Vacic et al. |
| 2018/0305135 A1* | 10/2018 | Kim ....................... B65G 47/06 |

FOREIGN PATENT DOCUMENTS

| | | | |
|---|---|---|---|
| JP | S58102161 A | 6/1983 | |
| JP | S62299768 A | 12/1987 | |
| JP | H03120471 A | 5/1991 | |
| JP | 06080174 | 11/1994 | |
| KR | 20180033940 A | 4/2018 | |
| WO | WO-0221144 A1 * | 3/2002 | ........... G01N 35/028 |
| WO | 2010036827 A1 | 4/2010 | |

\* cited by examiner

FLOW ASSAY ANALYZER

CROSS-REFERENCE TO RELATED APPLICATIONS

This application claims priority to U.S. provisional patent application 62/784,065, filed 21 Dec. 2018, and is a United States National Stage application under 35 U.S.C. 371 of PCT Application No. PCT/CA2019/051873, filed on 21 Dec. 2019, the contents of both of which are hereby incorporated by reference herein in their entirety.

FIELD OF THE INVENTION

The present invention pertains to the field of analytical chemistry and more particularly to a lateral flow assay device analyzer that supports concurrent diagnostic testing at a plurality lateral flow assay devices. The invention provides an integrated sample-processing system for high throughput preparing and analyzing of lateral flow assay samples.

BACKGROUND

Healthcare diagnostics laboratories use diagnostic instruments such as diagnostic analyzers for testing and analyzing samples. Healthcare professionals also utilize diagnostic instruments in point-of-care in clinics and other patient settings. One or more sample tubes or testing devices are typically placed into a rack or carrier and loaded into an analyzer by a technician or operator. Known diagnostic analyzers use various liquids and reagents to perform diagnostic analysis procedures. Analytical assays are useful in diagnostic applications, for example, in human health (e.g. blood and urine testing), environmental contamination (e.g. water and soil testing), and industrial food and drug preparation (e.g. bacterial contamination testing), but often require large and costly laboratory instruments and trained operators.

Lateral flow test strips based on the principles of immunochromatography exist for a wide array of target analytes. The first lateral flow tests were made for the detection of human chorionic gonadotropin and there are now commercially available immunological tests for monitoring ovulation, detecting infectious disease organisms, analyzing drugs of abuse, and measuring other analytes important to human physiology. Lateral flow assay products have also been introduced for veterinary testing, agricultural applications, environmental testing, and product quality evaluation. While the first lateral flow assay tests presented qualitative results based on the presence or absence of a signal line, test design has progressed toward semi-quantitative and quantitative assays with the integration of hand-held readers and high throughput analyzers. Most lateral flow test strips are modeled after existing immunoassay formats and are typically sandwich assays in which an antigen or compound of interest is immobilized between two layers of antibodies, a capture antibody and a detection antibody. In serum assays, antibodies are detected as indicators of various disease states and immunological status, and detect the formation of a complex between a detector particle that is free in the sample stream and a capture reagent that is bound to the membrane at a test line. Other microfluidic paper-based analytical devices, termed "µPADs", can perform more complex tests, as well as parallel multiplexing tests, in multiple flow directions (i.e. two and three dimensions, 2D & 3D) with narrower flow channel dimensions and, by extension, smaller required sample volumes than the common paper strip tests of the past. The ability to work with smaller volumes is important when testing samples that are difficult to acquire in large volume such as point-of-care tests for human health.

Attempts have been made to decrease sample turn-around time and process a multitude of lateral flow assay devices at a time to provide multiplex testing and improve throughput in assay testing and analysis. In one example, U.S. Pat. No. 9,389,228 to Jakubowicz et al. describes a metering mechanism that dispenses sample onto a lateral flow assay device, a radial incubator assembly having a plurality of receiving stations sized to individually receive a corresponding plurality of lateral flow assay devices, and a detection device for detecting test results on the lateral flow assay device. In another example, U.S. Pat. No. 8,883,509 to Lemme et al. describes an apparatus for continuous-access simultaneous processing of a plurality of individual substrate-supported biological samples having substrate holders arranged in a minor arc where the individual substrate support units are automatedly and independently movable between a separate processing position and a separate access position.

There remains a need for a robust high throughput analyzer for lateral flow assay testing and analysis.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a high throughput analyzer for lateral flow assay testing and analysis. Another object of the present invention is provide a combination cartridge system, analyzer and method for high throughput lateral flow analysis.

In an aspect there is provided an assay device analyzer comprising: a cartridge stage for releasably supporting an assay cartridge, the assay cartridge housing a lateral flow assay substrate; a fluid metering device; a detection device; at least one vertical support structure for vertically supporting a plurality of assay cartridges; an elevation adjustment mechanism coupled to the cartridge stage for vertical alignment of the elevation of the cartridge stage; and a translation adjustment mechanism coupled to the cartridge stage for translational alignment of the cartridge stage relative to the vertical support structure and the fluid metering device.

In one embodiment, the elevation adjustment mechanism and the translation adjustment mechanism are independent.

In another embodiment, the fluid metering device can be positionally adjusted to accommodate various configurations of the assay cartridge.

In another embodiment, the analyzer further comprises a second vertical support structure for vertically supporting a plurality of assay cartridges.

In another embodiment, the cartridge stage comprises a stage mount to releasably grip one or more elements on the assay cartridge.

In another embodiment, the analyzer comprises a detection device.

In another embodiment, the analyzer comprises more than one detection device.

In another embodiment, the detection device is a fluorimeter, spectrophotometer, colorimeter, camera, photomultiplier tube (PMT), charge coupled device (CCD) camera, digital camera using a complementary metal-oxide-semiconductor (CMOS) detector, laser, or photodiode.

In another embodiment, the fluid metering device is a sample metering device, running fluid metering device, or washing fluid metering device.

In another embodiment, the analyzer further comprises one or more additional fluid metering devices.

In another embodiment, the analyzer is enclosed in a housing.

In another embodiment, the housing comprises more than one assay device analyzer.

In another embodiment, the analyzer further comprises one or more temperature control device and humidity control device.

In another embodiment, the vertical support structure is a hopper

In another embodiment, the analyzer is a point-of-care analyzer, an automated clinical analyzer, or a combination thereof.

In another embodiment, the analyzer further comprises an electronic control system.

In another embodiment, the analyzer further comprises a quality check optical unit.

In another embodiment, there is provided a method for flow assay analysis, the method comprising: aligning a cartridge stage under a vertical support structure, the vertical support structure retaining a plurality of vertically disposed assay cartridges, each assay cartridge comprising an assay substrate with a detection area; elevating the cartridge stage to engage the cartridge stage with an assay cartridge retained in the vertical support; moving the cartridge stage with the engaged assay cartridge away from the vertical support structure and into alignment with a fluid metering device; metering fluid from the fluid metering device onto the assay substrate in the assay cartridge; incubating the assay cartridge; and detecting a component of the sample on a detection area of the assay substrate.

In an embodiment, the method further comprises, prior to incubating the assay cartridge, dispensing one or more additional sample, buffer, reagent, or detection component onto the assay substrate.

In another embodiment, the method further comprises controlling temperature and humidity around the analyzer.

In another embodiment, the method further comprises adjusting position of the fluid metering device and the detection device.

In another embodiment, the assay cartridge is moved by the cartridge stage to a second vertical support structure for incubation.

In another aspect there is provided an assay device analyzer comprising: a cartridge stage for supporting an assay cartridge, the assay device comprising a planar support having at least one sample addition area disposed upon said support, at least one reaction area, at least one detection area, and a wicking area fluidically interconnected along at least one lateral fluid flow path; a sample metering device; a detection device; a loading hopper for storing a plurality of assay cartridges; an elevation adjustment mechanism coupled to the cartridge stage for adjusting the elevation of the cartridge stage relative to the loading hopper; and a translation adjustment mechanism coupled to the cartridge stage for aligning the cartridge stage relative to the loading hopper, the sample metering device, and the detection device.

In another aspect there is provided a method for flow assay analysis, the method comprising: aligning, by elevation, a cartridge stage under a loading hopper, the loading hopper comprising a plurality of assay devices; engaging the cartridge stage with an assay device, the assay device comprising a planar support having at least one sample addition area disposed upon said support, at least one reaction area, at least one detection area, and a wicking area fluidically interconnected along at least one lateral fluid flow path; sliding the cartridge stage away from the hopper and into an alignment with a sample metering device; metering sample fluid from the sample metering device to the assay device; incubating the assay device; and detecting a component of the sample on the assay device.

BRIEF DESCRIPTION OF THE FIGURES

For a better understanding of the present invention, as well as other aspects and further features thereof, reference is made to the following description which is to be used in conjunction with the accompanying drawings, where.

DETAILED DESCRIPTION OF THE INVENTION

Figure 1A:
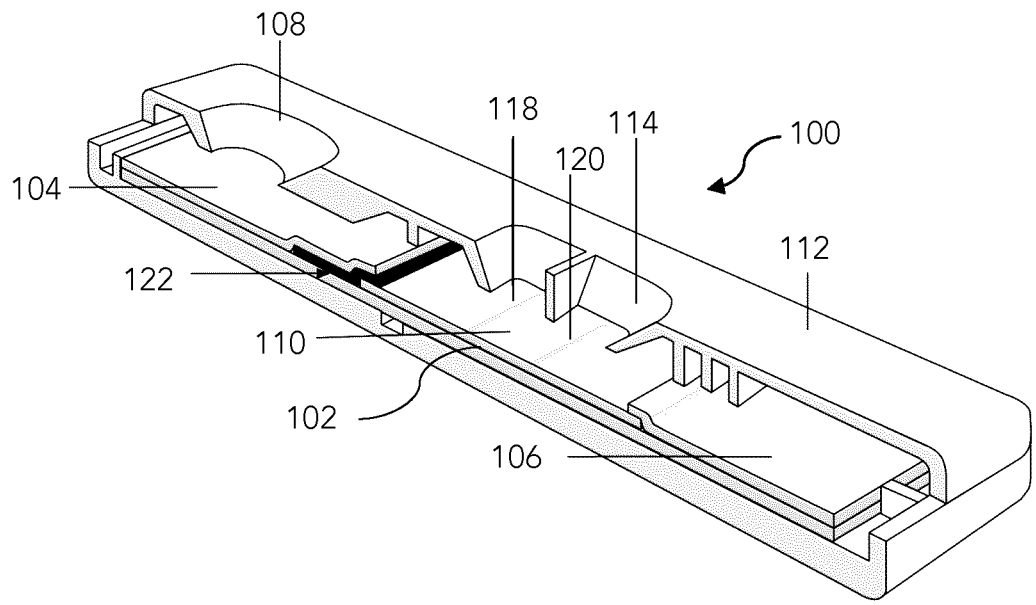
FIG. 1A is a perspective view of a prior art flow assay cartridge device.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or element(s) as appropriate.

The term "sample" as used herein, refers to a volume of a liquid, fluid, solution, or suspension, intended to be subjected to qualitative or quantitative determination of any of its properties or components, such as the presence or absence of a component, the concentration of a component, etc. Typical samples in the context of the present invention as described herein are derived from human or animal bodily fluids such as but not limited to blood, plasma, serum, lymph, urine, saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. Other non-limiting examples of samples that can be used are environmental samples, food industry samples, and agricultural samples.

The terms "test device" and "flow assay device" as used herein refers to any device that receives sample fluid and includes a fluid transport or flow path along which various areas or sites are provided for supporting one or more reagents, filters, and the like and through which sample traverses under the influence of capillary action or other forces. The fluid path can be laterally disposed, vertically disposed, or at any desired angle to achieve the best results. Test devices include but are not limited to thin-film or "dry slide" test elements, lateral flow assay devices, microfluidic paper-based analytical devices (μPADs), vertical flow assay devices, and chromatography devices, referred to generically herein as "flow assay devices".

The term "analyzer" as used herein, refers to any apparatus enabling the processing of various analytical test or flow assay devices, and in which a plurality of test devices can be processed. The analyzer further includes a plurality of components configured for loading, incubating, testing, and evaluating a plurality of analytical test elements in automated or semi-automated fashion and in which test elements are automatically dispensed and processed substantially without user intervention. Analyzers include but are not limited to clinical diagnostic apparatus and point-of-care type devices.

The term "reaction" as used herein, refers to any interaction which takes place between components of a sample and at least one reagent or reagents on or in, or added to, the substrate of the test device, or between two or more components present in the sample. The term "reaction" is used to define the reaction taking place between an analyte and a reagent on the test device as part of the qualitative or quantitative determination of the analyte.

The terms "substrate" or "support" refers to the carrier or matrix to which a sample is added, and on or in which the determination is performed, or where the reaction between analyte and reagent takes place.

Described herein is a lateral flow assay analyzer for preparing and analyzing flow assay samples. The analyzer supports concurrent diagnostic testing at a plurality of flow assay devices and provides an integrated and robust sample-processing system with concurrent testing. The analyzer is designed to support the use of a plurality of flow assay devices such that a plurality of tests can be incubated and processed concurrently. A sample metering device is provided to apply a metered amount of sample to each of a plurality of test devices. Each flow assay device can also have a different bound reactant to test for a different component in the sample fluid and can be labelled to identify its contents. The present design offers a significant reduction in analyzer size and reduces overall foot print while providing a system for testing a plurality of components in the sample.

One advantage to the present system is that the herein described flow assay analyzer does not require the separate addition of wet reagents. In particular, dried reagents can be already incorporated into the structure of each flow assay device such that a sample fluid can be added, optionally together or sequentially with an additional running fluid or buffer, thereby allowing for automated multi-test handling. Room temperature storage of the lateral flow assay devices and can also enable extended shelf life. Additionally, lateral flow devices and μPADs require only very low volumes of sample and other fluids and can be used with the present analyzer. Further, each flow assay device processed by the analyzer can be prepared with different reagents and conjugates to detect a different component of the sample, enabling a multitude of sample components to be tested at the same time. Applications of the herein described flow assay devices may also include the direct use of whole blood, thereby providing reduced overall processing times with no requirement for centrifugation. In other uses, samples can be diluted with an appropriate buffer and high efficiency detection methods can be used with diluted samples. By employing the flow assay devices in the herein described analyzer, overall reaction times that can be traditionally as high as one hour with standard non-automated devices can be effectively reduced, preferably to a range of within five to ten minutes. The presently described automated flow assay device analyzer can be used in clinical as well as point-of-care analyzer applications, and can reduce overall costs in instrumentation and point-of-care sample processing. By further enabling sample multiplexing on a single flow assay device, detections of multiple reactants can be run simultaneously on a single flow assay device, thereby creating lower cost per test and significantly higher effective throughput. Multiplexing can significantly increase throughput by the effective multiplexing factor and can be as high as 10 times (or more).

The described flow assay device analyzer can enable the incorporation of various internal controls and calibrations, thereby providing means to ensure calibration, quality of the result, reproducibility, and the ability to track assay degradation over time. These features further provide means for incorporation with other intelligent reliability systems, such as provided on automated clinical analyzers. Still another advantage is that factory or wet calibration stability allows a factory calibration to simplify user operation. The presently described analyzer can also increase calibration intervals to typical general chemistry intervals and provide commonality of formats between point-of-care (POC) and mainframe assays, providing development improvement. As such, an assay can be enabled to be used in both types of applications (POC and mainframe), providing higher production volumes and economies of scale. The foregoing therefore ensures quality results and equal performance in both the POC and mainframe markets. Thin film elements and flow assay cartridge devices can be used on the analyzer with minor adjustments to the analyzer stage mount, vertical support structure, and metering and detector positioning, wherein the form factor of the flow assay devices permits their use interchangeably with thin film dry slide elements and an expansive number of already existing flow assay devices. Versatility is significantly enhanced wherein systems can be realized that can incorporate thin-film analytical test elements, lateral flow assay devices as described herein and conventional wet chemistry systems or portions thereof in a single unit.

In a scenario where each cartridge is unique in terms of bound reactants but the sample in the sample metering device is the same, the analyzer is simplified and each cartridge can be labeled, optionally with a barcode, that is detectable with an identification detection unit, optionally an optical unit. In this case of each cartridge having a different binding conjugate, a single sample (such as blood) can be added to the sample addition area with each cartridge measuring a different component in the sample and the cartridges can be optically tracked as they traverse through the analyzer from dry, to running (incubation), to analysis. In another example, sample can be pre-loaded onto each cartridge and the metering mechanism can apply an amount of liquid, such as buffer or other running fluid, to each cartridge to elute the sample. An identification device can be further fitted to the analyzer, such as, for example, a barcode reader.

A variety of flow assay devices with a variety of assay substrates can be used with the presently described automated flow assay analyzer in a clinical, analytical, and/or a point-of-care setting. To that end, it will be readily apparent to one of skill in the art that the inventive concepts herein described are equally applicable to a myriad of other flow assay device designs and use in various other types of automated, as well as point-of-care diagnostic clinical analyzers. Still further, the automated analyzers described herein can be configured, for example, to handle a variety of flow assay devices without requiring the separate inclusion of dry slide analytical elements as a stand-alone assembly and alternatively to include other analytical systems in addition to those for the handling of lateral flow assay devices, as described herein, such as in a conventional wet chemistry or chromatography analytical system. The presently described analyzer can be adapted to accommodate a wide variety of cartridge style high throughput devices which use liquid additional lateral flow processing and detection, such as, for example, chromatography or slides, vertical flow assay devices, paper-based microfluidic analytical devices (µPADs), blot assays, microfluidic cartridges, and can also be equipped to handle conventional immunoassays, chemistry assays, as well as testing of thin film analytical test elements. The shape and size of the assay device is not particularly restricted, and may be any shape and size suitable for the utility for which it is intended, and the analyzer may be adapted to accommodate any size or shape of assay device. A plurality of lateral flow assay devices can be used in conjunction with the lateral flow assay analyzer. A set of lateral flow assay devices can be interchangeable in the analyzer and sets comprising a plurality of lateral flow assay devices can be easily loaded into the analyzer for parallel processing by the analyzer.

Assay design using lateral flow devices can be highly varied based on matrix or substrate materials and configuration, liquid components and order of addition, and timing of the assay. Persons skilled in the art will be aware that multiple types of species can be used for lateral flow assays including but not limited to visualization species, detection elements, labels or labeled binding species, conjugate species, detergents, blocking reagents, analytes, enzymes, binding partners, capture elements, control species, and other detectable materials. Lateral flow devices are also most often, though not required to be, used for immunoassays, and generally include one or more antibody and antigen. Each of the species in the assay can be either suspended in liquid for addition to the solid matrix, or applied to the solid matrix such that dissolution or suspension by an added liquid promotes movement of the species along the matrix and binding with other species. A multitude of assay designs are known that vary the location and formulation of each of the assay species. On the solid matrix the species can be arranged in various locations along the flow path and in various dot or line configurations, and can be individually placed or mixed with other components, with optional pre-mixing in a liquid and addition to the matrix and drying of the matrix prior to use. Species can also be formulated in the flow buffer or in other liquid formulations for addition to the solid matrix at an appropriate time based on the assay design. The type and timing of liquid or reagent addition as well as the relative positions of solid components on the matrix can also greatly affect the outcome and sensitivity of an assay, and a wide variety of configurations and combinations of binding assay design are known in the art and available to the skilled person as options for assay optimization.

The following exemplary embodiments relate to the configuration and design of a lateral flow assay device for use in an automated lateral flow assay analyzer as herein described. FIG. 1A shows an exemplary lateral flow assay device 100. The lateral flow assay device 100 in accordance with this embodiment is defined by a planar substrate 102 which is preferably made from a suitable porous or non-porous material with surface properties that support capillary like flow. In some embodiments, the planar substrate 102 can comprise flow channels, optionally cut into the surface of the substrate. A sample addition area 104 at one side of the lateral flow assay device 100 extends to at least one detection area 110 and preferably a wicking area 106. The sample addition area 104 disposed at one end of the lateral flow assay device 100 forms a portion of a fluid flow path extending through a detection area 110 containing a detection conjugate or other reagent to detect reaction with one or more components in the sample. Wicking area 106 at the opposite end of the fluid flow path draws sample fluid in the desired direction along the flow assay device 100. Optionally, the fluid flow path may also include additional separate areas containing reagents or detection conjugate, as well other areas or sites along this path that can be utilized used for washing of the sample and any bound or unbound components thereof. Sample can be added to the test device through sample port 108, and results or reaction can be detected through results port 114. A defined fluid flow path is created from the sample addition area 104 extending to the wicking area 106, which is optionally at least partially open. In another embodiment, the flow path is entirely open. By "open" what is meant is that there is no lid or cover at a location above the planar assay substrate. Thus a lid, if present as a physical protection for the flow path, is not required to contribute to the capillary flow in the flow path. In another embodiment the planar substrate 102 is almost entirely encapsulated by a cartridge 112 or housing, enabling sample addition at the 104 sample addition area and detection of reaction at the 110 detection area through apertures in the cartridge lid. A cartridge 112 can house and protect the flow assay device 100 and provide robustness for transport and movement of the flow assay device 100 in the analyzer. A solid cartridge 112 is further capable of being moved by the moving mechanism of the analyzer without damage to the planar substrate 102 and detection area within. The cartridge 112 can comprise a cartridge bottom, cartridge side walls, and cartridge end walls to provide additional solidity and durability to the lateral flow assay device. A cover or lid can be optionally included. A results port 114 in the cartridge is positioned around the detection area 110 to enable one or more detector to detect reaction in the detection area 110. Various configurations of lateral flow assay devices are known, including but not limited to variation in device dimensions, materials, porosity of the substrate, presence or absence of topographical features on the substrate, channel shape and configuration, and method of manufacturing the channel. The particular lateral flow assay device 100 is referred to throughout this description in terms of an exemplary embodiment, however it will be readily apparent that other device designs and possible variants of these designs could also be similarly configured for interrelationships in a clinical analyzer, as herein discussed.

The lateral flow assay device 100 is defined by a planar substrate 102 that includes a sample addition area 104 that receives sample from a liquid dispenser or sample metering device. When the lateral flow assay device 100 is encapsulated by a cartridge 112 or cartridge housing, sample from the liquid dispenser is placed on the sample addition area 104 through a sample port 108. The sample is typically deposited onto the top of the sample addition area 104, and the sample addition area 104 is capable of transporting the liquid sample from the point when the sample is deposited to a reagent area through a conjugate pad 122. Once fluid is added to the sample addition area 104 or upstream the sample addition area 104, the planar substrate promotes spontaneous lateral capillary flow along the defined fluid flow path between the sample addition area 104 and the wicking area 106. The lateral flow assay device can also comprise an optional filter material (not shown) which can be placed within the sample addition area 104 to filter particulates from the sample or to filter blood cells from blood so that plasma can travel through the device. After the sample has been delivered to the sample addition area 104, it will encounter the conjugate pad 122. After the sample has flowed through and interacted with the conjugate pad 122 and optionally the reagent addition area, the sample and a reagent plume will be contained in the fluid flow. The reagent plume can contain any of the reagent materials that have been dissolved in the conjugate pad 122 or those added through the optional reagent addition area. The reagent plume can include the conjugate having both the detection element and binding partner, in which case it is often referred to as a conjugate plume. Downstream from the detection area 110 along the fluid path is the wicking area 106 in fluid communication with the detection area. The wicking area 106 is an area of the assay device 100 with the capacity of receiving liquid sample and any other material in the flow path, such as for example unbound reagents, wash fluids, etc. The wicking area 106 provides a capillary force to move the liquid sample through and out the detection area of the assay device. The wicking area can include a porous material such as, for example, nitrocellulose. The wicking area can further include non-capillary fluid driving means, such as using evaporative heating. Optionally a hydrophilic foil or layer can be positioned directly onto at least a portion of the wicking area 106 to enhance the overall flow rate or process time of a sample applied to the flow assay device.

Components of the flow assay devices such as the physical structure of the device, whether or not a discrete piece from other parts of the device, described herein can be prepared from, for example, copolymers, blends, laminates, metallized foils, metallized films or metals, waxes, adhesives, or other suitable materials known to the skilled person. Alternatively, device components can be prepared from copolymers, blends, laminates, metallized foils, metallized films or metals deposited on any one or a combination of the following materials: paraffins, polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, other polymers, glass, and ceramic materials. Alternatively, components of the flow assay device can be made with a plastic, elastomer, latex, silicon chip, or metal. In one example, the elastomer can comprise polyethylene, polypropylene, polystyrene, polyacrylates, silicon elastomers, or latex. Alternatively, components of the device can be prepared from latex, polystyrene latex or hydrophobic polymers. In one example, the hydrophobic polymer can comprise polypropylene, polyethylene, or polyester. Alternatively, components of the device can comprise TEFLON®, polystyrene, polyacrylate, or polycarbonate. Alternatively, device components can be made from plastics which are capable of being embossed, milled or injection molded or from surfaces of copper, silver and gold films upon which may be adsorbed various long chain alkanethiols. The structures of plastic which are capable of being milled or injection molded such as the cartridge housing can comprise, for example, a polystyrene, a polycarbonate, a polyacrylate, or cyclo-olefin polymer.

The defined flow path of assay devices described herein, including device 100, can include open or closed paths, channels, grooves, and capillaries for directing fluid flow along the fluid flow path. Conjugate pad 122 can optionally be placed between the sample addition area 104 and the detection area 110 to fluidly connect these elements. An optional reagent addition area between the sample addition area 104 and the detection area 110 can also allow the addition of a reagent externally from the device. For example, the reagent addition area may be used to add an interrupting reagent that can be used to wash the sample and other unbound components present in the fluid flow path into a wicking area 106. Reagent can either be added in the reagent area prior to use and potentially dried on the reagent area, added to the reagent area just prior to use using a reagent metering device on the analyzer, or both. The reagent can also be added via an optional reagent metering device. Reagents include but are not limited to binding partners such as antibodies or antigens for immunoassays, DNA and RNA aptamers with or without resonance energy transfer (RET) pairs and respective target analytes, substrates for enzyme assays, probes for molecular diagnostic assays, and auxiliary materials such as materials that stabilize the integrated reagents, materials that suppress interfering reactions, and the like. Generally, one of the reagents useful in the reaction bears a detectable signal as discussed herein. In some cases, the reagents may react with the analyte directly or through a cascade of reactions to form a detectable signal such as a colored or fluorescent molecule. In one preferred embodiment, the reagent area includes conjugate material. The term "conjugate" means any moiety bearing both a detection element and a binding partner. In use, a fluid sample is introduced to the sample addition area 104 in the device, and will flow within the fluid flow region to one or more detection or test areas 110. The detection or test area includes one or more reagents reactive with or useful to detect a target component within the sample area.

For the purposes of this description, a detection element is an agent which is detectable with respect to its physical distribution and/or the intensity of the signal it delivers. Examples of suitable detection elements for use with the presently described assay device include but are not limited to luminescent molecules such as fluorescent agents, phosphorescent agents, chemiluminescent agents, bioluminescent agents and the like, colored molecules, molecules producing colors upon reaction, enzymes, radioisotopes, and ligands exhibiting specific binding and the like. The detection element, also referred to as a label, is preferably chosen from chromophores, fluorophores, radioactive labels, and enzymes. Suitable labels are available from commercial suppliers, providing a wide range of dyes for the labeling of antibodies, proteins and nucleic acids. There are, for example, fluorophores spanning practically the entire visible and infrared spectrum. Suitable fluorescent or phosphorescent labels include for instance, but are not limited to, fluoresceins, Cy3, Cy5 and the like. Suitable chemiluminescent labels include but are not limited to luminal, cyalume and the like. Similarly, radioactive labels are commercially available and detection elements can be synthesized so that they incorporate a radioactive label. Suitable radioactive labels include but are not limited to radioactive iodine and phosphorus; e.g., $^{125}$I and $^{32}$P. Suitable enzymatic labels include but are not limited to horseradish peroxidase, beta-galactosidase, luciferase, alkaline phosphatase and the like. Some other examples of detectable materials include but are not limited to colloidal gold, enzyme conjugates, other colloidal metals, fluorescent particles, and magnetic particles. Two or more labels may be used, for example, when multiple analytes or markers are being detected. The binding partner is a material that can form a complex that can be used to determine the presence of or an amount of an analyte. For example, in a "sandwich" assay, the binding partner in the conjugate can form a complex including the analyte and the conjugate, and that complex can further bind to another binding partner, also called a capture element, integrated into the detection area. In a competitive immunoassay, the analyte will interfere with binding of the binding partner in the conjugate to another binding partner, also called a capture element, integrated into the detection area. Example binding partners included in conjugates include, for example, antibodies, antigens, analyte or analyte-mimics, and other proteins.

The detection area 110 is where any detectable signal can be read on test line 118 and control line 120. The width in the flow path in the detection area 110 is typically on the order of 0.044-4 mm and preferably on the order of about 2 mm, although others can be prepared on the order of about 1 mm, provided sufficient signal for a suitable detection instrument can be read. Capture elements in the detection area 110 can hold binding partners for the conjugate or complexes containing the conjugate, as described above. For example, if the analyte is a specific protein, the conjugate may be an antibody that will specifically bind that protein to a detection element such as fluorescence probe. The capture element could then be another antibody that also specifically binds to that protein. In another example, if the marker or analyte is DNA, the capture molecule can be, but is not limited to, synthetic oligonucleotides, analogues, thereof, or specific antibodies. Other suitable capture elements include antibodies, antibody fragments, aptamers, and nucleic acid sequences, specific for the analyte to be detected. A non-limiting example of a suitable capture element is a molecule that bears avidin functionality that can bind to a conjugate containing a biotin functionality. The detection area can also include multiple detection areas and include one or more markers.

Figure 1B:
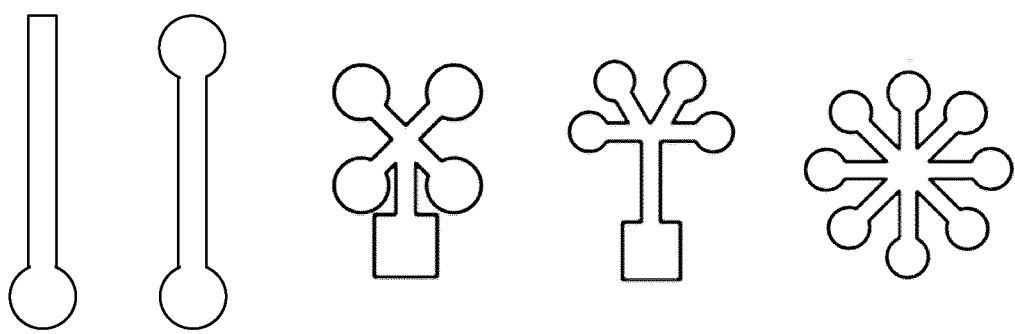
FIG. 1B is a view of various prior art flow assay micropad type devices.

FIG. 1B is a view of various prior art lateral flow assay micro paper-based analytical devices, also referred to as micropad (µPAD) type devices, which is one type of lateral flow assay device that can be used with the present analyzer. µPAD assay devices have a sample addition zone or area and can have one or more reaction zones for detection of one or more components of the sample. µPAD substrates are widely used in analytical chemistry as they provide an inexpensive and user-friendly analytical process amenable to miniaturization and small sample volumes. In the event of multiple detection areas, the capture elements can include multiple capture elements, such as first and second capture elements.

The conjugate can be pre-deposited on the assay device, such as by coating in the reagent area. Similarly, the capture elements can be pre-deposited on the assay device on the detection area. Preferably, both the detection and capture elements are pre-deposited on the assay device, or on the reaction area and detection area, respectively. Capture elements, such as antibodies in the detection area (such as by coating) and a labeled conjugate material that is also capable of participating in reactions that will enable determination of a concentration of analyte, are preferably deposited on the device downstream the sample addition area 104, wherein the labeled conjugate material carries a label for detection in the detection area.

Examples of applications of the presently described analyzer include but are not limited to, biomedical diagnostics such as pregnancy tests, glucose tests, biomarker tests, environmental testing such as water testing for microbial or other contaminants (e.g. arsenic). Fluid samples that may be analyzed using the present device include but are not limited to water or water-containing samples from various sources (e.g. tap, well, pond/lake, wastewater, rainwater, etc.), and bodily fluids such as blood, urine, saliva, sweat, tears or amniotic fluid. Sample volumes for use with the present analyzer may vary. In particular, the analyzer and device may be sized to accommodate sample sizes in the microliter range, such as samples of less than 1000 µL, and less than 10 µL, including samples of less than 1 µL.

Antibodies used in immunochromatographic tests must have sufficient sensitivity, specificity, purity, and stability to accomplish the performance requirements of the finished product. Depending on the assay design, antibodies may be used as a capture reagent at the test line, as a conjugate on the detector particle, or both. Purification and consistency of supply are also important. Since the antibodies may be bound to a membrane and detector particle, proteins will compete for binding sites. There is also the decision to be made as to whether polyclonal or monoclonal antibodies will be used. Minimally, the antibody preparation should be affinity-purified. Any ligand recognition system where a detector particle becomes bridged to a capture reagent on the membrane can be used.

Figure 2:
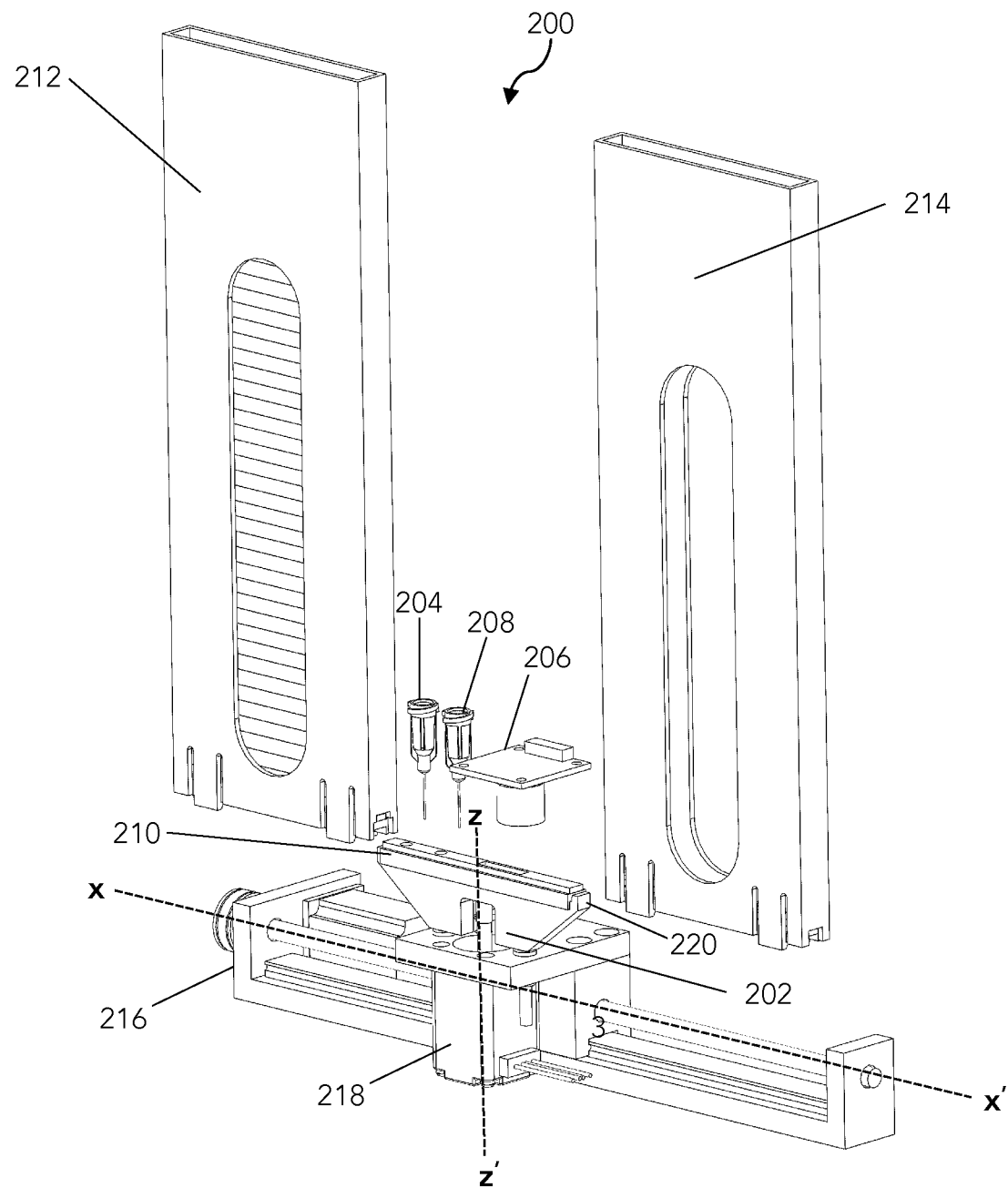
FIG. 2 is a front perspective view of a flow assay analyzer.

FIG. 2 is a front perspective view of a flow assay analyzer 200 comprising a translatable cartridge stage 202, a fluid metering device 204, and a detection device 206. The translation adjustment mechanism 216 is functionally connected to the cartridge stage 202 to move the cartridge stage along axis x-x' in the plane of the analyzer components. It is also conceivable that a further translation adjustment mechanism and associated mechanical components can be integrated to provide translation of the cartridge stage 202 along a y-axis, normal to the x-x' and z-z' axes as shown. The translation adjustment mechanism 216 can be comprised of a hydraulic actuator, an electric motor in combination with a worm drive gear system, movable track and gear, electric servo motor, or any other translation mechanism known to the skilled person. The elevation adjustment mechanism and the translation adjustment mechanism can be independent mechanisms that control the elevation and translation independently. Alternatively, the elevation adjustment mechanism and the translation adjustment mechanism can be a single mechanism that can control both translation and elevation movements of the cartridge stage.

One or more vertical support structure is configured for vertically supporting a plurality of assay cartridges in the assay analyzer. The minimum requirements for a vertical support structure include maintaining the position of the cartridges in such a way that the assay cartridges can be removed from the vertical support structure one at a time and providing features to ensure only the desired number of cartridges are removed from the stack or added to the stack with the desired shuttling motion of the cartridge stage. The vertical support structures can be, for example, a vertical support enclosure such as a hopper, one or more plates in combination with one or more rails to guide the vertical position of the cartridges, and at a minimum, a base plate or base support structure to locate the cartridge stack and a retention mechanism hold the cartridge stack stationary while enabling and guiding the desired cartridge to be moved by the cartridge stage. Optionally, the analyzer can comprise a single vertical support structure wherein movement of the assay stage can allow cartridges to be added to the top of a cartridge stack in the vertical support structure such that the first cartridge ends up back at the bottom once all of the cartridges in the stack have been cycles through the analyzer and the one or more vertical support structures. The assay analyzer can further have one or more additional shuttling mechanisms or cartridge stages with associated translation and elevation mechanisms. The one or more vertical support structures are optionally removable or reversibly engageable from the assay analyzer such that assay cartridges can be loaded and/or removed more easily. A vertical support structure can also be pre-loaded with assay cartridges for easy handling by technicians and optionally disposable. The vertical support structures will be referred to in the described embodiments as hoppers, however it is understood that other configurations of vertical support structures as described may be substituted in the presently described embodiments. Loading hopper 212, which serves as a vertical support structure, stores a plurality of assay device cartridges for use in the analyzer in a vertical orientation such that cartridge stage 202 can be aligned to the bottom of the vertical support structure or loading hopper and stage mount 220 can releasably grip a single flow assay device cartridge and slide the cartridge out of the loading hopper 212. Stage mount can comprise, for example, one or more guides, posts, clips, friction devices, or any other features that enable reversible attachment to the bottom of an assay cartridge 210. In other embodiments, cartridge stage 202 can be adapted to receive more than one assay cartridge 210.

Fluid metering device 204 can be comprised of a syringe with a pump, for example a hydraulic or electrical motor or servo motor with appropriate metering gears or movement devices or fluid metering pump, for metering out aliquots of fluid sample onto the assay substrate inside assay cartridge 210. Sample is preferably metered to the sample area by a syringe operated by controlled mechanical actuation with no or minimal contact to prevent aerosolizing the sample fluid. Fluid metering device 204 preferably has an attached metering tip which can be aligned with the sample port of assay cartridge 210 by adjusting the height of cartridge stage 202 using elevation adjustment mechanism 218. The elevation adjustment mechanism and the translation adjustment mechanism shown are independent, however they may also be a single translation device capable of effecting both translational and elevational adjustment to the cartridge stage. The fluid metering device 204 can optionally be fitted with metering tip which is optionally disposable. The analyzer 200 can also optionally have one or more additional or secondary metering device 208 for metering a second fluid to the assay device, or a plurality of metering devices as required. Examples of fluid and fluid components which can be metered onto the assay substrate include but are not limited to samples, diluted samples, buffers, reagents, binding agents, dyes, etc. The assay device analyzer can also include more than two liquid metering tips each connected to the same or different liquid reservoir or liquid supply, with each reservoir or supply containing the same or different liquid composition for addition to the solid matrix or assay substrate. Each liquid metering tip can be configured to deliver, for example, assay solution comprising one or more components, optionally further comprising one or more assay species, with each metering tip capable of delivering a liquid component or composition to the lateral flow assay device at the desired time. As previously discussed, a wide variety of solid matrix assay designs and configurations are possible, and can be accommodated by the presently described flow assay analyzer.

An electronic control system comprising a microcontroller in or connected to the assay device analyzer can also be configured to control one or more of the electronic controls, motors, and pumps of the flow assay analyzer including but not limited to control of movement and location of components, order of addition of liquid components, volume of liquid addition, timing of movement or liquid addition, speed of movement, liquid addition, and detection device control including detection parameters. The control system can further be controlled or set using a local or remote user interface or control device which can be enabled to control addition of fluid to the assay device according to the desired assay design, and can comprise a memory and input device for receiving and storing data pertaining to the assay design and conditions. The control system can be configured to communicate with one or more user interfaces by connecting to the control system, said user interfaces can include by are not limited to a remote terminal, desktop, laptop, tablet, smartphone, or smart electronic device. The control system can be further connected to a communication network through a wired or wireless connection, such as, for example, a wi-fi enabled connection device, bluetooth connection device, or other communication enabled device. The electronic control system can also optionally be further in communication with a processor connected to, wired or wirelessly, the detection device. Each of the fluid metering device 204 and the one or more secondary metering devices 208 can further be connected to the electronic control system for controlling one or more of the volume, timing, and location of addition of fluid onto the assay matrix or onto the assay device. Once sample has been added to the assay cartridge 210 by fluid metering device 204, translation adjustment mechanism 216 translationally aligns cartridge stage 202 under incubation hopper 214, which serves as a second vertical support structure, where the assay cartridge device can be stored during incubation. In the embodiment where there is a single vertical support structure, the translation adjustment mechanism and the elevation adjustment mechanism can move the assay cartridge to deposit it back into the single vertical support structure, preferably at the top of the vertical support structure, such that the next assay cartridge can be removed from the bottom of the vertical support structure. As used here, the term "incubation" refers to the time between addition of sample or running fluid to the planar substrate and the time when the detectable components are bound with the detection area. Incubation time can also be thought of as the time required between sample and/or buffer addition and the time when the assay device results can be obtained. Incubation time will vary depending on the size and nature of the planar substrate and flow assay device materials, thicknesses, and sizes used.

After incubation, detection device 206 attached to a detection instrument is capable of detecting the perceivable signal of the detection area of the flow assay device and visualizing the results of the flow assay. The detection device 206 is disposed and aligned to scan the test area of flow assay devices that are caused to be positioned within an adjacent test area. The detection device 206 is preferably electronically connected to a processor for image processing. Other detection devices can be used with the present analyzer, examples of which include but are not limited to a fluorimeter, spectrophotometer, colorimeter, camera, photomultiplier tube (PMT), charge coupled device (CCD) camera, digital camera using a complementary metal-oxide-semiconductor (CMOS) detector, laser, and photodiode. In one example, a camera equipped with single or an array of LEDs is used to optically scan the devices one at a time along a portion of the fluid flow path and more preferably along the linear portion of the flow channel separating the sample addition area and the wicking area and preferably containing the detection area and depending on the construction of this element, at least one reaction area including a test line and also preferably a control line. These detection methods amongst others can be used in combination with, for example, lenses, optical filters, or any other optical method for improving the signal or ratio of signal to noise of the detected signal.

The cartridge stage 202 is capable of receiving at least one flow assay device. The cartridge stage 202 grips and holds the assay device via features in the stage mount 220 and aligns the flow assay device with the sample metering device, detection device and the vertical support structures during incubation and analysis. The stage mount 220 can be also designed to accommodate a variety of cartridge configurations, or to be interchangeable on the cartridge stage 202 such that it can releasably engage various different cartridges. Lateral flow assay cartridges are dispensed from the lower opening of loading hopper 212 by releasable engagement with the stage mount 220 and securably retained within or on top of stage mount 220 on cartridge stage 202 for transport in the assay analyzer. Stage mount 220 can engage a bottom and/or side or lateral edge of the assay cartridge 210 in order to releasably grip and translatably move same. Any physical configuration of stage mount and assay cartridge wherein the stage mount can releasably and securably hold the assay cartridge can be used, including but not limited to features for snapping, sliding, or gripping engagement. The assay cartridges are shuttled back and forth on the cartridge stage 202 by the translation adjustment mechanism into the metering and detection area, with assay cartridges preferably moved from the loading hopper 212 to the metering area 202 one at a time. Elevation adjustment mechanism 218 is functionally connected to the cartridge stage 202 and moves the cartridge stage up and down along axis z-z' to align the cartridge stage 202 and stage mount 220 with the loading hopper 212, incubation hopper 214, such that the stage mount 220 can engage and disengage each assay cartridge, and align the assay cartridge by one or more sample metering devices and one or more detection devices. Hoppers 212 and 214 situated adjacent the cartridge stage are capable of holding a plurality of stored lateral flow assay devices. A plurality of hoppers and/or other vertical support structures may also be used as needed. The location of the metering device relative to the stage, reservoirs, detection device, and other features and the relative locations of the metering device and detection device can be adjusted to accommodate for different lateral flow assay device configurations and different distances between sample addition area and detection area, as well as cartridge or device dimensions such as device width and length. The analyzer can comprise one or more metering device, to deliver more than one sample, reagent, buffer, or other fluid to the device. The fluid delivered by the metering device can comprise any aqueous or non-aqueous fluid, optionally including sample, buffer, reagent, and/or detection component. The flow assay analyzer can further be housed in a housing which provides temperature and/or humidity control, and the housing can further comprise one or more heaters, coolers, and/or humidity control devices. The housing can also accommodate one or more than one flow assay analyzer device.

Figure 3:
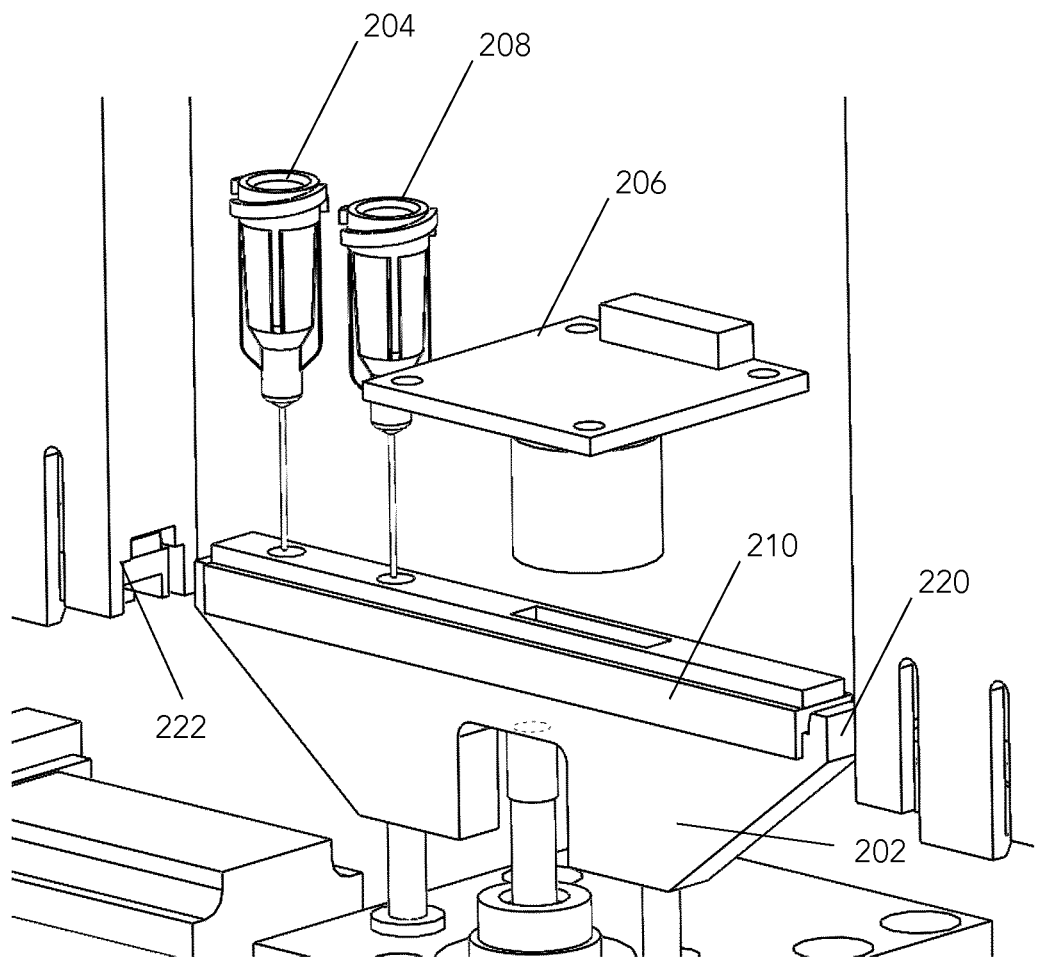
FIG. 3 is a closeup perspective view of a flow assay analyzer showing dispensing and detection devices.

FIG. 3 is a closeup perspective view of a flow assay analyzer showing dispensing and detection devices, with closeup around the metering and detection area of the analyzer. The vertical support structure stores a plurality of vertically stacked assay cartridges, and each assay cartridge 210 can be individually removed one at a time by sliding through the side aperture 222 of the vertical support structure after engagement of the bottom of the assay cartridge 210 with the stage mount 220 on the cartridge stage 202 through the side of the vertical support structure. The stage mount 220 has features that releasably interact with and hold the bottom of each assay cartridge 210 such that the assay cartridge can be slid out of the vertical support structure along translational axis x-x' using a translation mechanism. As shown in FIG. 3, when the analyzer is in use, the assay cartridge is engaged with the stage mount 220 and slidingly removed from the vertical support structure via a translation adjustment mechanism, after which the cartridge stage 202 is translationally aligned along axis x-x' and vertically aligned along axis z-z' with an elevation adjustment mechanism such that the sample port of the assay cartridge is aligned with fluid metering device 204 where sample is applied to the assay cartridge 210 through the sample port. Optional secondary metering device 208 provides a fluid dispensing system for dispensing a secondary fluid to the assay cartridge as required for the individual assay being run, and can optionally align with a secondary metering port on the assay cartridge. Detection device 206 is shown positioned adjacent the fluid metering device 204 however can be in any location where the assay cartridge can be positioned into alignment by the translation adjustment mechanism and the elevation adjustment mechanism for effective detection.

Figure 4:
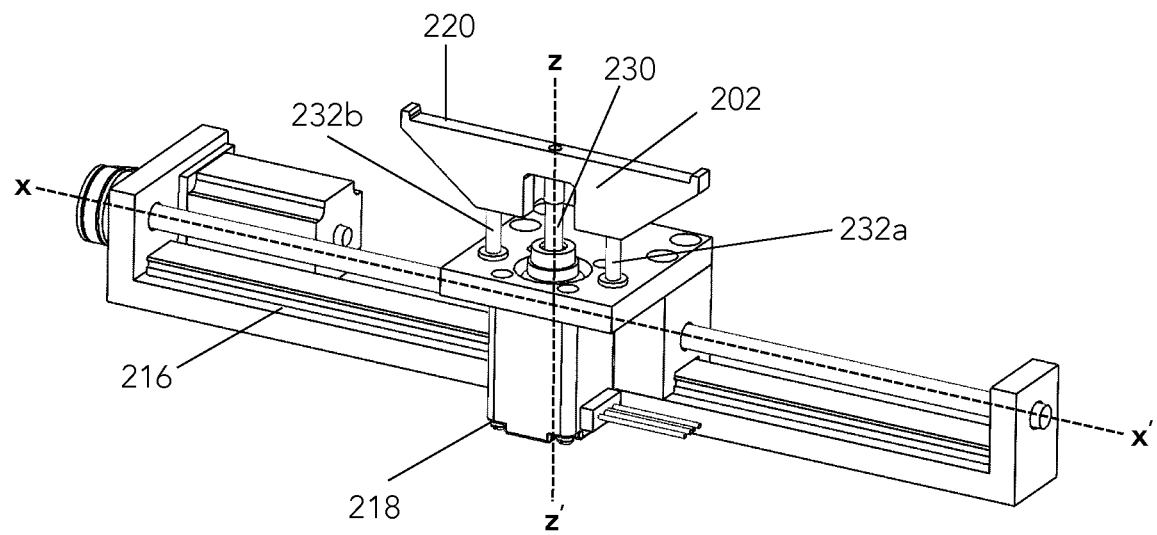
FIG. 4 is a front perspective view of an analyzer translation adjustment mechanism, elevation adjustment mechanism, and cartridge stage.

FIG. 4 is a front perspective view of one example of an analyzer translation adjustment mechanism 216, elevation adjustment mechanism 218, and cartridge stage 202. Elevation adjustment mechanism 218 has a motor or other mechanism to move the cartridge stage 202 with stage mount 220 up and down along axis z-z' by functional connection with an elevation stem 230. Optional alignment posts 232a and 232b assist with controlling vertical alignment of the cartridge stage 202 and preventing misalignment of the cartridge stage 202 from the x-x' axis. A housing for the elevation adjustment mechanism 218 can provide further guides in the form of slots, holes, or elongated apertures for guiding the up and down motion and alignment of the alignment posts 232a and 232b and elevation stem 230 to maintain accurate positioning of the cartridge stage 202 in the analyzer.

Figure 5:
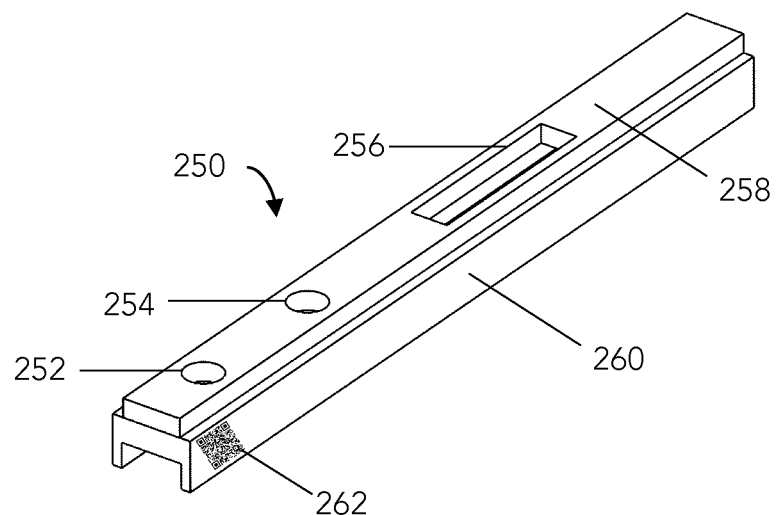
FIG. 5 is a perspective view of a closed assay cartridge.

FIG. 5 is a perspective view of an example closed assay cartridge 250 for use with the presently described analyzer. The assay cartridge 250 comprises a cartridge body 260 with a bottom and side walls which is capable of being loaded with a thin film analytical test element or substrate. The assay cartridge shown has an optionally removable cartridge lid 258 comprising sample port 252 for receiving fluid sample, secondary fluid port 254 (optional, based on the requirements of the assay), and results port 256 for providing an opening through which the assay results can be detected by a detector. The assay cartridge 250 can also have one or more optional barcode 262, which can be any digital data stored as an image that can be read by an optical reader. Alternatively, the assay cartridge can have one or more other identification tags such as, for example, an RFID tag or electromagnetic label.

Figure 6:
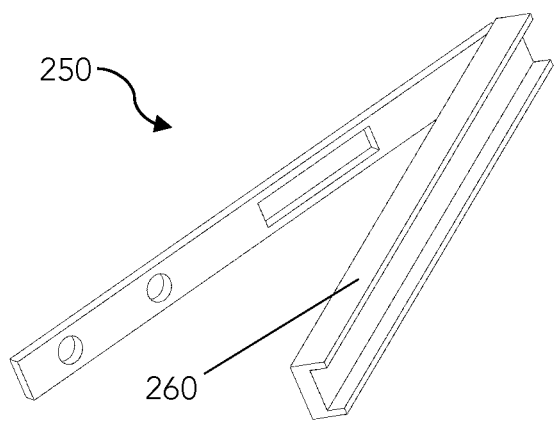
FIG. 6 is a perspective view of the bottom of an assay cartridge.

FIG. 6 is a perspective view of the bottom of an assay cartridge 250 with cartridge body 260. The features of the bottom of the assay cartridge enable engagement with the stage mount for holding the assay cartridge such that the cartridge stage can align the assay cartridge device with the sample metering device and the detection device. In the embodiment shown, the assay cartridge has two flexible arms that engage with the stage mount, allowing the cartridge to be snapped into place. These same flexible arms also allow the cartridge to slide onto or off of the stage mount.

Figure 7:
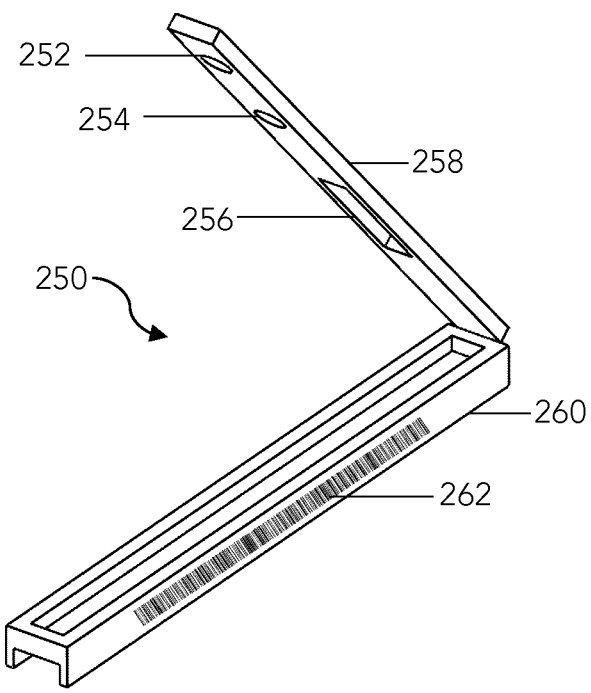
FIG. 7 is a perspective view of an open assay cartridge.

FIG. 7 is a perspective view of an open assay cartridge 250 with the cartridge lid 258 open and angled relative to the cartridge body 260 with an optional barcode 262. Also shown in the cartridge lid are sample port 252, optional secondary fluid port 254, and results port 256.

One exemplary method is herein described involving the testing of at least one lateral flow assay device in the assay analyzer 200. FIGS. 8 to 13 sequentially demonstrate the analyzer movement in this example method as assay cartridges are shuttled through the analyzer from storage to sample dispensing to incubation to analysis. Starting with FIG. 8, which is a closeup view of the elevation mechanism and alignment of the raised cartridge stage under the loading hopper, the translational adjustment mechanism aligns the cartridge stage under the loading hopper which is loaded with assay cartridges. Once aligned, the elevation adjustment mechanism adjusts the height of the cartridge stage by raising the elevation stem along the z-z' axis to put the stage mount on the cartridge into alignment with the bottom of the bottommost assay cartridge in the loading hopper as shown by the arrow. The bottom of the assay cartridge positively engages with features on the stage mount 220 to support transport of the assay cartridge on the stage mount 220 throughout movement of the assay cartridge in the analyzer. Assay cartridges are dispensed from a lower side opening of the loading hopper and retained within the stage mount on the cartridge stage.

Figure 9:
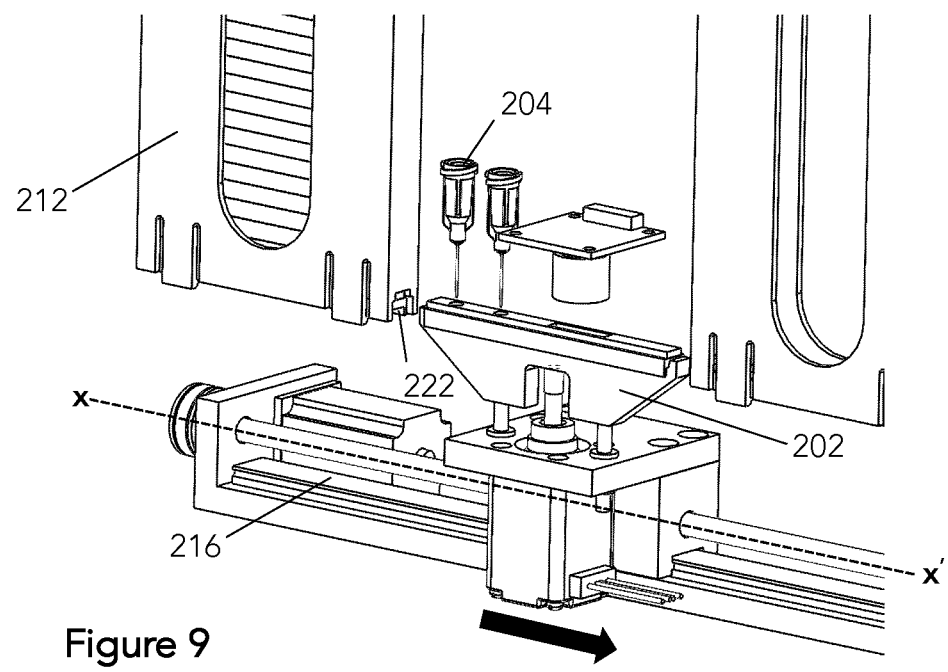
FIG. 9 is a view of a flow assay analyzer with cartridge stage holding a cartridge and translated under the dispensing and detection device.

FIG. 9 is a closeup view of the analyzer with cartridge stage holding a cartridge and translated under the dispensing and detection device. As shown in FIG. 9, once the stage mount is positively engaged with the bottom side of the assay cartridge, the cartridge stage 202 is shuttled laterally along the x-x axis to slide the assay cartridge out of the loading hopper through hopper side aperture 222, in the direction as shown by the arrow. Assay cartridges are translationally shuttled back and forth along the x-x' axis, with assay cartridges preferably moved from the loading hopper 212 to the cartridge stage 202 one at a time. Adjacent the loading hopper is a metering area of the analyzer comprising the fluid metering device 204 and optionally comprising one or more secondary metering devices. The translation adjustment mechanism 216 shuttles the lateral flow assay device cartridge on the cartridge stage 202 into the metering area such that the assay cartridge is positioned within the confines of a sample addition area and the sample port of the cartridge is aligned with the fluid metering device 204. A volumetric portion of the sample contained within the metering tip is then dispensed onto the dry slide test element to begin flow in the flow assay device.

Figure 10:
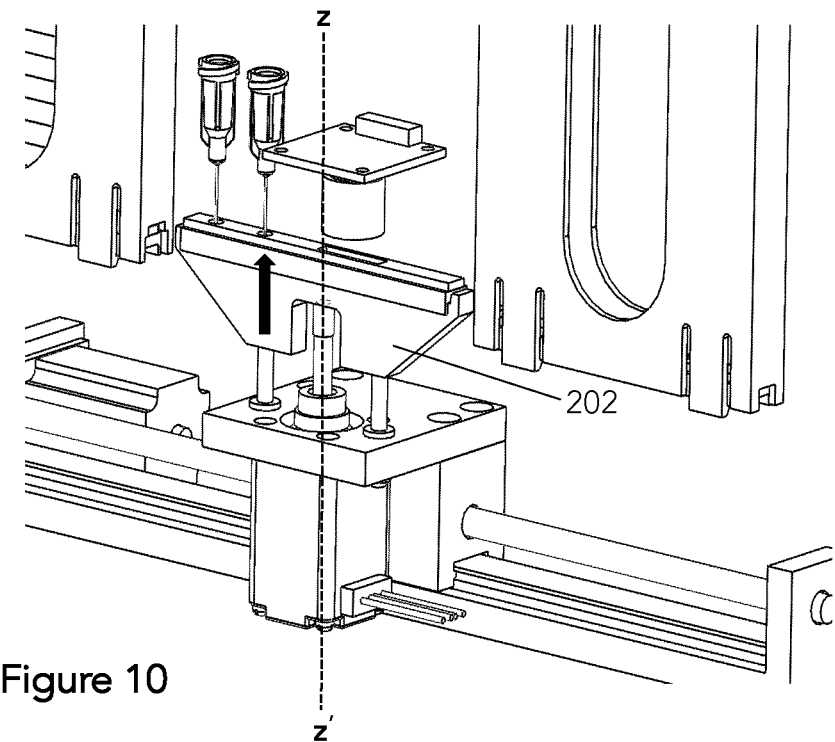
FIG. 10 is a view of the analyzer with raised cartridge stage aligned under the dispensing and detection device.

FIG. 10 is a closeup of the analyzer with raised cartridge stage aligned under the dispensing and detection device. Once aligned under the metering area, the assay cartridge is moved into position and aligned along the z-z' axis with the sample metering device using elevation adjustment to the cartridge stage 202 provided by the elevation adjustment mechanism. A predetermined volume of sample is then deposited onto the sample addition area of the lateral flow assay device. Based on the design of the lateral flow assay device, the application of sample to the sample addition area either spontaneously induces lateral capillary flow of the dispensed patient sample along the defined flow path or can be started with addition of additional running fluid. In the assay device, sample then flows from the sample addition area under the capillary force created along the flow path extending through the reaction area on the substrate.

Figure 11:
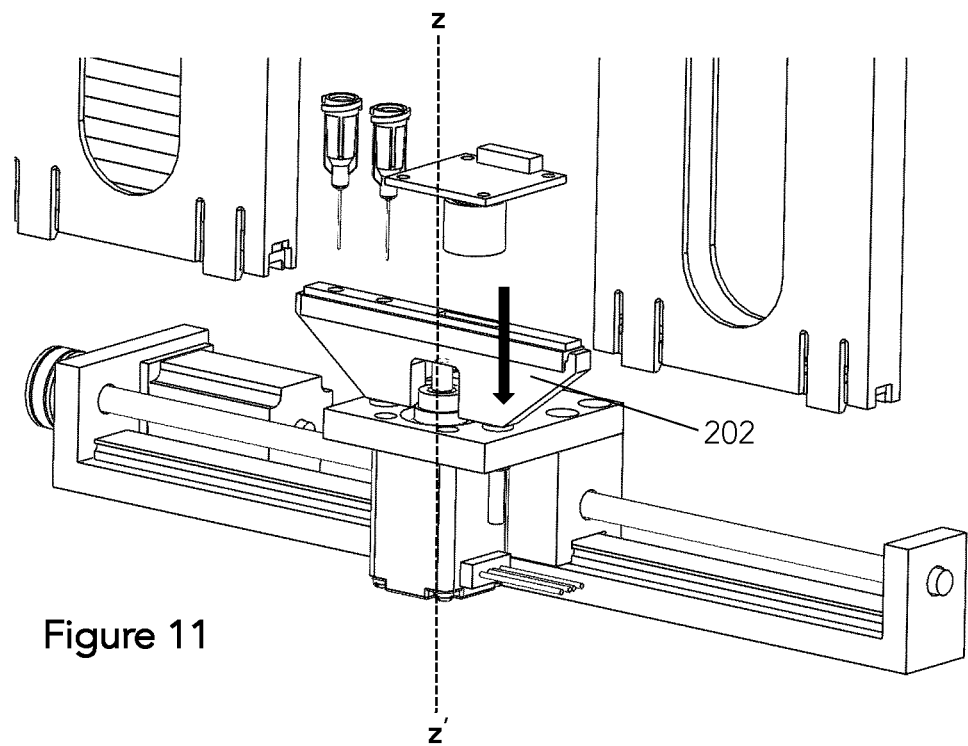
FIG. 11 is a view of the analyzer with lowered cartridge stage.

FIG. 11 is a closeup of the analyzer with lowered cartridge stage after sample addition. As the fluid sample first engages the detection conjugate or other reagent, the sample begins to dissolve this conjugate, thereby creating a perceivable plume indicative of the process flow, such as a conjugate plume. The elevation adjustment mechanism then lowers the cartridge stage 202 along the z-z' axis below the level of the incubation hopper to allow the translation adjustment mechanism to slide the cartridge stage 202 under the incubation hopper.

Figure 12:
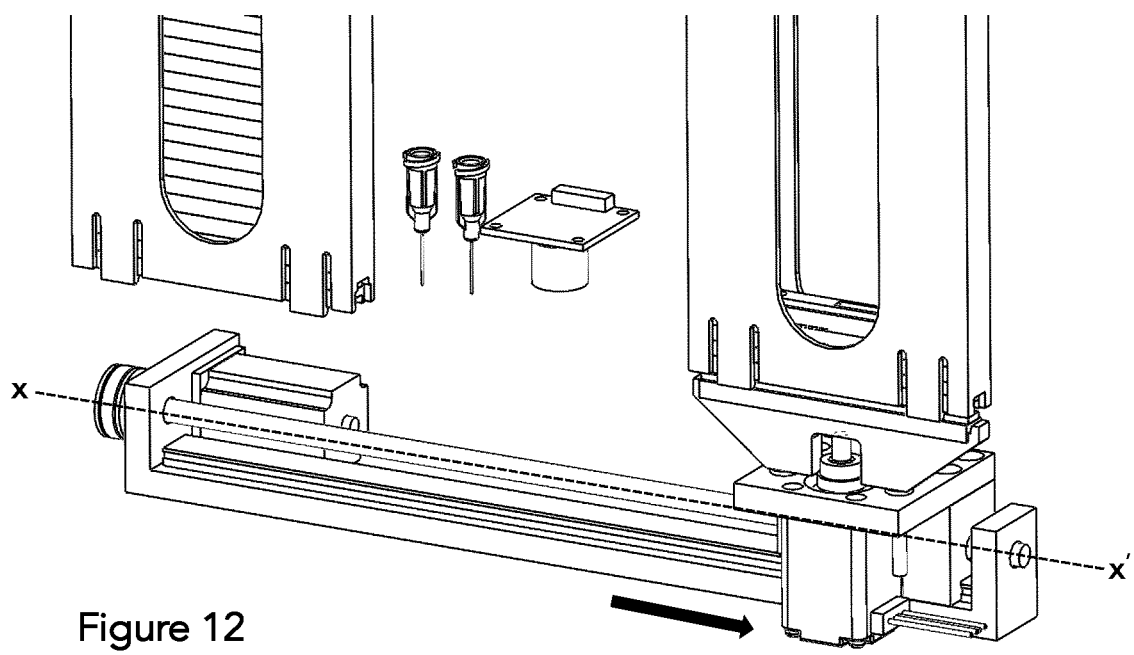
FIG. 12 is a view of the analyzer with cartridge and stage translated to an incubation hopper.

FIG. 12 is a closeup of the analyzer with cartridge and stage translated along the x-x' axis to the incubation hopper. During incubation the sample and related material advance towards the detection area and the wicking area of the assay device. The fluid sample continues to flow along the flow path and along any intermediate reaction areas, enabling a reaction to take place, which can be detected by the detection device. The sample continues to advance to the wicking area, the latter being sized to receive the volume of fluid dispensed. The flow assay device is then incubated for a predetermined time based on the flow assay device and assay being conducted.

Figure 8:
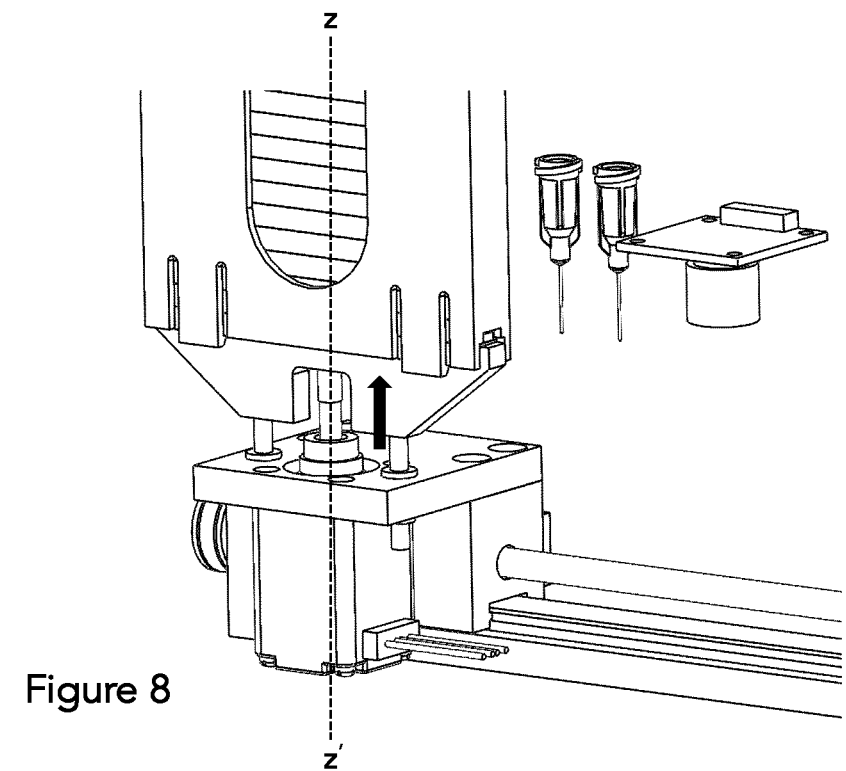
FIG. 8 is a view of the elevation adjustment mechanism and alignment of the raised cartridge stage under a loading hopper.
Figure 13:
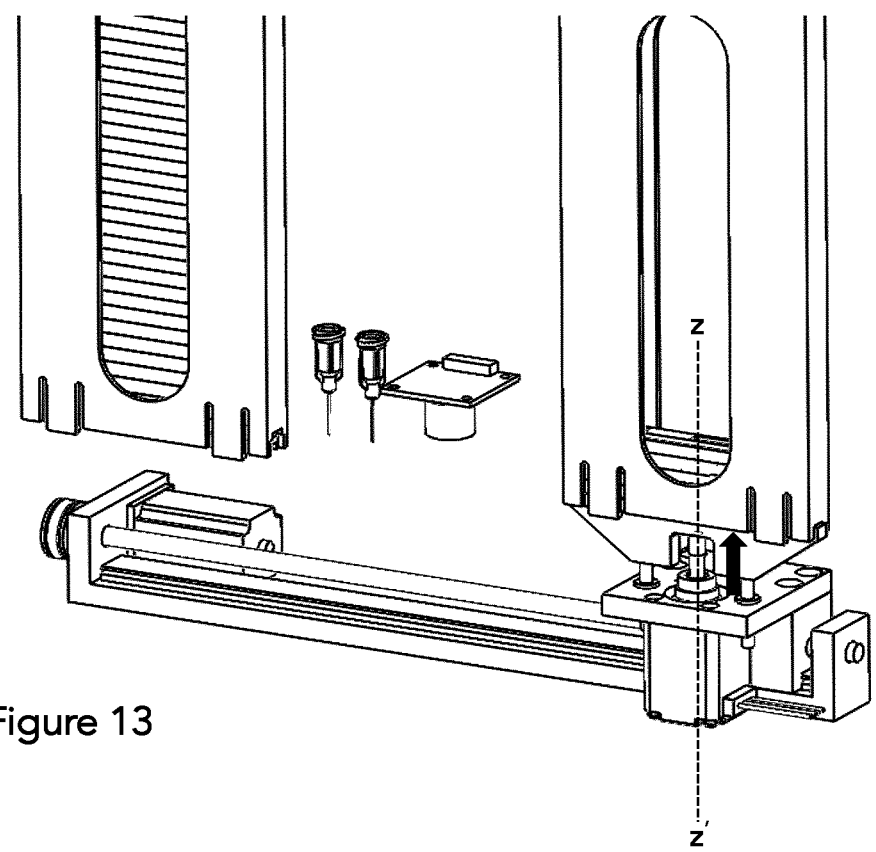
FIG. 13 is a view of the analyzer with stage raised relative to the incubation hopper.

FIG. 13 is a closeup of the analyzer with stage raised along the z-z' axis relative to the incubation hopper to deposit the assay cartridge into the incubation hopper until the assay cartridge is removed for reading. An aperture in the bottom of the incubation hopper receives the assay cartridge from below and features in the lower part of the incubation hopper retain the assay cartridge. Assay cartridges are retained in the incubation hopper for a predetermined dwell time or incubation time depending on the number and types of tests to be performed on the assay device and elution or detection time required for the assay. Following a predetermined incubation time (e.g., 5 minutes, 10 minutes, etc.) the analyzer aligns the cartridge stage and stage mount to the lowermost assay cartridge in the incubation hopper and slidingly removes the assay cartridge from the incubation hopper through a side aperture in the incubation hopper in a similar way as shown in FIGS. 8 and 9 in respect of the loading hopper. Once the assay cartridge is translationally adjusted under the detection device the results are read to permit detection scanning of the contained sample and reactants along a portion of the flow path that aligns the detection area of the assay device. Optionally, the elevation adjustment mechanism can be used to align the assay cartridge in an optimal position for detection at the detection area on the assay cartridge. Once detection is complete the cartridge is removed from the cartridge stage for processing of further assay cartridges. In one example, the assay devices can be slid off of the cartridge stage and caused to drop through a vertically disposed exit chute (not shown) to be discarded. Assay test instrumentation with an appropriate detection device can determine the results of the assay, which can include presence and/or concentration of analyte in the sample solution. Analyte detection with the detection device allowing analytical test or detection results can be therefore be provided in real time. Further analysis, optionally using prediction algorithms, can be processed in an on-board or connected computer.

Figure 14:
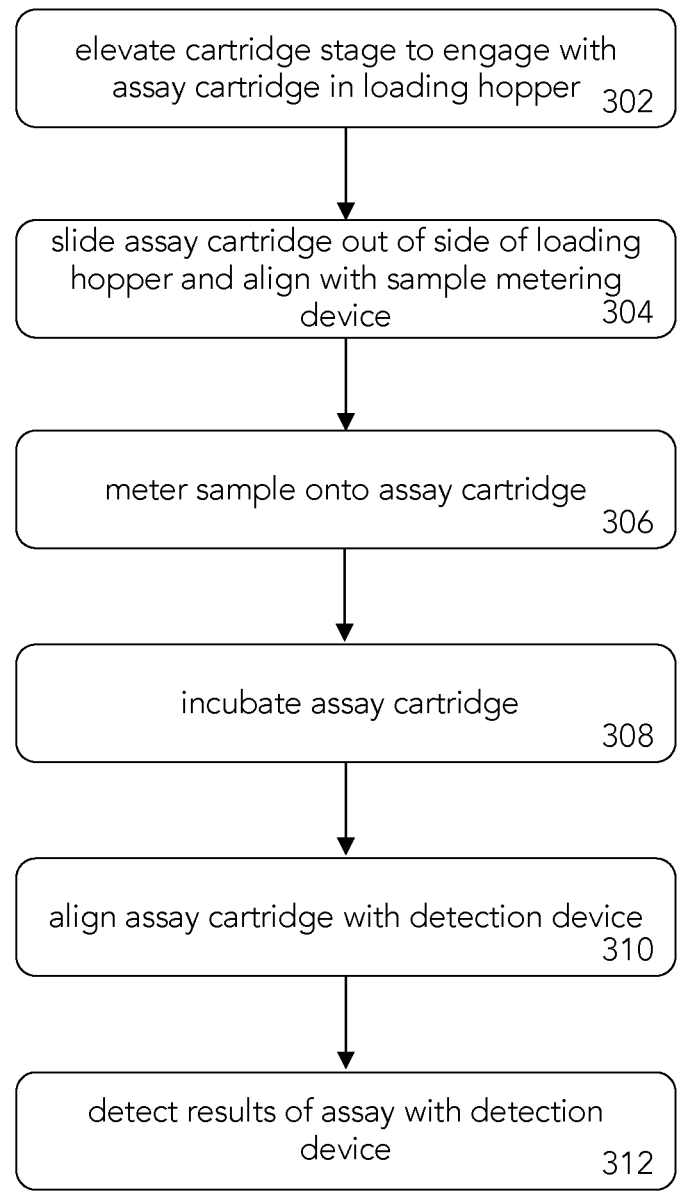
FIG. 14 is a flowchart of a method of using the analyzer.

FIG. 14 is a flowchart of a method of using the analyzer. First the stage mount on the cartridge stage is elevated to engage with the bottom of an assay cartridge stored in the loading hopper 302. Once engaged, the cartridge stage with engaged assay cartridge slides out of the side of the loading hopper and aligns with sample metering device 304. The sample is then metered onto assay cartridge 306 wherein a known quantity or volume of sample is deposited onto the assay matrix or substrate element. The assay cartridge is then allowed to incubate for a determined amount of time depending on the assay 308. Once incubated the assay cartridge is aligned with detection device 310 and the results of the assay are detected with the detection device 312 wherein the test instrumentation determines the results (analyte concentration, detection, etc.). Incubation of one or more assay cartridge can occur while other cartridges are being loaded with sample to provide a streamlined method of performing multiple assays during the same time period. In this embodiment the cartridges under incubation can be loaded to a second hopper, and once sample has been added to all the cartridges, all of the cartridges can be moved back to the first hopper such that each cartridge can be removed and the results read by the detector in order of sample addition.

The presently described flow assay analyzer can also comprise a quality check (QC) optical device unit. Quality check optical devices can be used for a variety of purposes in an automated flow assay analyzer including but not limited to identification and/or verification of unique assay cartridges, and confirmation that the correct amount and quality of sample and/or reagent has been added to the flow assay substrate. The optical unit for quality check can be independent of or used in concert with the detection device to detect assay results as well as the progression of the analytical device or parts thereof, or movement of assay cartridges through the analyzer. The quality check optical unit can comprise one or more optical detection devices for optical interrogation and detection of aspects of the flow assay process, including one or more cameras, scanners, and detection means for monitoring and quality checking the various steps carried out by the high throughput flow assay analyzer. In some non-limited examples, the optical unit can have an individual or an array of photodetectors, such as, for example, comprising one or more photoresistors, photodiodes, phototransistors, complementary metal oxide semiconductor (CMOS) image sensors, and/or charge coupled device (CCD) image sensors. The optical unit can further comprise one or more light source such as, for example, one or more light emitting diode (LED), light bulb, mercury lamp, and laser. A data reader LED can also be used as an optical data reader to detect and read encoded digital data on an assay cartridge such as barcode data, QR (Quick Response) code data, or other identifying marks to positively identify the assay cartridge housing. The QC optical device can also store and read data related to the cartridge handling while the assay cartridge is in the analyzer, the data including but not limited to volumetric data of sample and reagent addition, buffer addition, addition and analysis times, and this collected data can be correlated with other data such as, for example, reagent and sample batch information, patient information, assay and substrate configuration and/or setup information, and other information relevant to the assay to provide additional quality data for each assay. The optical unit can also optionally one or more passive optical components such as, for example, one or more lens assembly, mirror, prism, diffuser, optical fiber, waveguide, collimator, beam splitter, optical grating, polarizer, and one or more optical filter such as short-pass, band-pass, long-pass, band-rejection, notch filter, or other optical filter. The QC unit can also do process checks on one or more object or device in the flow assay analyzer, including but not limited to the sample syringe, secondary or reagent syringe, syringe cap, syringe plunger, sample quality or quantity in the syringe, the positioning or state of the test cartridge, the barcode on the cartridge, the size and physical characteristics of the sample or reagent dispenser sample droplet, and the housing/fixture that holds the abovementioned components. In one example, the optical unit can detect changes in the sample and/or reagent fluids by measuring one or more of fluid color, turbidity, reflectance, volume, and droplet size or shape. The QC unit can also be used to determine the presence of sample syringe, the presence and positions of the syringe cap and/or plunger, the presence of syringe needle holder, the presence, position, and/or volume of air bubbles and/or air gaps inside the sample or fluid metering device or any additional sample or fluid metering device, the volume of sample, the color and/or color uniformity of the sample, the presence and volume of dispensed sample droplet, the presence and volume of dispensed reagent, the presence and position of cartridges, and the barcode information on the cartridge. An optical unit in position proximity with a fluid metering device can monitor, detect, record, and potentially provide feedback regarding fluid conditions in the metering devices in the analyzer. In one example configuration, the QC optical unit consists of one or more light source and one or more optical detector at the ends of the optical path, and the object or device to be checked is between the light source and the optical detector along the optical path. The optical detector can detect photons from the light source reflected by and/or transmitted through and/or generated by the object. The optical path can be in free space or inside or at the surface of, reflected by, or deflected by the passive optical components in different sequences and/or combinations depending on the nature of the light source and the optical detector. Various combinations of light sources and optical detectors can also be used. The optical unit can also monitor fluid metering devices to monitor fluid dispensing such as by monitoring fluid or droplet size and/or characteristics and general fluid flow inside the fluid metering devices such as air gap(s) and/or air bubbles which can occur in syringe-type metering devices and result in false negatives in the assay if insufficient sample is metered onto the assay substrate. When the concentrations and volumes of sample used are small to enable high throughput, errors in metering can lead to poor results and lack of quality and reproducibility. Similar occurrences can result from air bubbles or gaps in the reagent metering system or device and in any running fluid or buffer metering device. The quality control optical unit can thereby monitor one or more of the fluids being delivered to ensure fluid quality and correct quantity to improve reproducibility and confidence in the results.

All publications, patents and patent applications mentioned in this specification are indicative of the level of skill of those skilled in the art to which this invention pertains and are herein incorporated by reference. The invention being thus described, it will be obvious that the same may be varied in many ways. Such variations are not to be regarded as a departure from the scope of the invention, and all such modifications as would be obvious to one skilled in the art are intended to be included within the scope of the following claims.

The invention claimed is:

1. An assay device analyzer comprising:
   a cartridge stage for releasably engaging a lateral flow assay cartridge, the cartridge stage comprising a stage mount with features to releasably grip one or more elements on the bottom of an assay cartridge, the assay cartridge housing a lateral flow assay substrate;
   first and second vertical support structures for vertically supporting a plurality of vertically stacked lateral flow assay cartridges, the first and second vertical support structures comprising:
      a base support structure for supporting the plurality of vertically stacked lateral flow assay cartridges comprising features in the lower part of the vertical support structure to retain the assay cartridges and having an aperture in the bottom to allow engagement of a bottommost assay cartridge in the vertical support structure by elevation of the stage mount on the cartridge stage and positive engagement of the bottom of the assay cartridge with the features on the stage mount;
      a side aperture for enabling sliding of the bottommost cartridge into and out of the vertical support structure after engagement of the bottommost assay cartridge with the stage mount and translation of the stage mount away from the side aperture such that each assay cartridge can be individually removed one at a time by sliding through the side aperture of the vertical support structure after engagement of the bottom of the assay cartridge with the stage mount on the cartridge stage through the side of the vertical support structure that the side aperture is located on; and
      a retention mechanism configured to hold the plurality of vertically stacked lateral flow assay cartridges stationary while enabling the bottommost assay cartridge to be moved out of the side aperture by the cartridge stage;
   a fluid metering device disposed between the first and second vertical support structures;
   an elevation adjustment mechanism coupled to the cartridge stage to move the cartridge stage up and down on an axis z-z' for vertical alignment and elevation of the cartridge stage under the first and second vertical support structures; and
   a translation adjustment mechanism coupled to the cartridge stage for translational alignment of the cartridge stage along a translational axis x-x' normal to the axis z-z' relative to the first and second vertical support structures and the fluid metering device,
   wherein once the stage mount is positively engaged with the bottom of an assay cartridge in one of the first and second vertical support structures, the cartridge stage can be shuttled laterally along the x-x' axis to slide the assay cartridge out of the vertical support structure through the side aperture.

2. The analyzer of claim 1, wherein the fluid metering device can be positionally adjusted to accommodate various configurations of the assay cartridge.

3. The analyzer of claim 1, further comprising a detection device.

4. The analyzer of claim 3, comprising more than one detection device.

5. The analyzer of claim 3, wherein the detection device is a fluorimeter, spectrophotometer, colorimeter, camera, photomultiplier tube (PMT), charge coupled device (CCD) camera, digital camera using a complementary metal-oxide-semiconductor (CMOS) detector, laser, or photodiode.

6. The analyzer of claim 1, wherein the fluid metering device is a sample metering device, running fluid metering device, or washing fluid metering device.

7. The analyzer of claim 1, further comprising one or more additional fluid metering devices.

8. The analyzer of claim 1, wherein the analyzer is enclosed in a housing.

9. The analyzer of claim 8, wherein the housing comprises more than one assay device analyzer.

10. The analyzer of claim 1, further comprising one or more temperature control devices and/or one or more humidity control devices.

11. The analyzer of claim 1, wherein the vertical support structure is a hopper.

12. The analyzer of claim 1, wherein the analyzer is a point-of-care analyzer, an automated clinical analyzer, or a combination thereof.

13. The analyzer of claim 1, further comprising an electronic control system.

14. The analyzer of claim 1, further comprising a quality check optical unit.

15. A method for flow assay analysis, the method comprising:
   aligning a cartridge stage under a vertical support structure having a bottom aperture, the vertical support structure retaining a plurality of vertically disposed assay cartridges, each assay cartridge comprising an assay substrate with a detection area, the cartridge stage comprising a stage mount to releasably grip one or more elements on the assay cartridge;
   elevating the cartridge stage on a vertical z-z' axis to engage the cartridge stage through the bottom aperture of the vertical support structure with a bottommost assay cartridge retained in the vertical support structure, the bottommost assay cartridge having a cartridge bottom for positively engaging with features on the stage mount to support transport of the assay cartridge on the stage mount;
   moving the cartridge stage with the engaged assay cartridge through a side aperture in the vertical support along a translational axis x-x' normal to the vertical axis z-z' and away from the vertical support structure and into alignment with a fluid metering device;
   metering fluid from the fluid metering device onto the assay substrate in the assay cartridge;
   incubating the assay cartridge; and
   detecting a component of the sample on the detection area of the assay substrate with a detector.

16. The method of claim 15, further comprising, prior to incubating the assay cartridge, dispensing one or more additional sample, buffer, reagent, or detection component onto the assay substrate.

17. The method of claim 15, further comprising controlling temperature and humidity around the vertical support structure.

18. The method of claim 15, further comprising adjusting position of the fluid metering device and the detector.

19. The method of claim 15, wherein the assay cartridge is moved by the cartridge stage to a second vertical support structure for incubation.

* * * * *